United States Patent
Schlachter et al.

(12) 
(10) Patent No.: US 6,471,969 B1
(45) Date of Patent: Oct. 29, 2002

(54) TWO-PHASE PREPARATION

(76) Inventors: Herbert Schlachter, Kolumbusstrasse 7, D-81543 Munich (DE); Michael Hamm, Heimweg 6, D-20148 Hamburg (DE)

(*) Notice: Subject to any disclaimer, the term of this patent is extended or adjusted under 35 U.S.C. 154(b) by 0 days.

(21) Appl. No.: 08/983,637

(22) PCT Filed: Jul. 29, 1996

(86) PCT No.: PCT/EP96/03329

§ 371 (c)(1),
(2), (4) Date: Mar. 30, 1998

(87) PCT Pub. No.: WO97/04668

PCT Pub. Date: Feb. 13, 1997

(30) Foreign Application Priority Data

Jul. 28, 1995 (EP) .......................................... 95111978

(51) Int. Cl.[7] .............................. A61K 9/20; A61K 9/48; A61P 3/02
(52) U.S. Cl. ...................... 424/400; 424/452; 424/465
(58) Field of Search ................... 424/422, 423, 424/432, 451, 452, 456, 464, 465, 484, 439, 460, 400

(56) References Cited

U.S. PATENT DOCUMENTS

| | | | |
|---|---|---|---|
| 4,070,488 A | * | 1/1978 | Davis |
| 4,466,958 A | * | 8/1984 | Morrison |
| 4,876,097 A | * | 10/1989 | Morrison ..................... 426/74 |
| 4,938,984 A | * | 7/1990 | Traitler et al. |
| 5,073,373 A | * | 12/1991 | O'Leary et al. ............ 424/422 |
| 5,514,382 A | * | 5/1996 | Sultenfuss |
| 5,518,730 A | * | 5/1996 | Fuisz ........................ 424/426 |
| 5,877,289 A | * | 3/1999 | Thorps ....................... 530/387 |

FOREIGN PATENT DOCUMENTS

| | | |
|---|---|---|
| EP | 57093913 | 6/1982 |
| EP | 0146474 A2 | 6/1985 |
| EP | 0216419 A3 | 4/1987 |
| EP | 0216419 A2 | 4/1987 |
| EP | 0224157 A1 | 6/1987 |
| EP | 0296751 A1 | 12/1988 |
| EP | 0366480 A2 | 5/1990 |
| EP | 0366480 A3 | 5/1990 |
| EP | 0409559 A3 | 1/1991 |
| EP | 0409559 A2 | 1/1991 |
| FR | 2394292 | 1/1979 |
| HU | 166966 | 11/1975 |
| HU | 204981 | 10/1990 |
| HU | 63751 | 11/1991 |

OTHER PUBLICATIONS

Abstract and claims from Chinese Patent CN 1088734A (93100603.1), Inventors: An Hou Run, Pub Date: Jul. 06, 1994.

English translation of the relevant parts of Hungarian patent 63751 Nov. 1, 1991.

English translation of the relevant parts of Hungarian patent 166966 Nov. 28, 1995.

English translation of the relevant parts of Hungarian patent 204981 Mar. 10, 1990.

* cited by examiner

Primary Examiner—Edward J. Webman
(74) Attorney, Agent, or Firm—Birch, Stewart, Kolasch & Birch, LLP

(57) ABSTRACT

The invention relates to a two-phase preparation for use at differential times and comprising a product A for the first phase and a product B for the second phase which comprise, independently of each other, at least one representative of the unsaturated fatty acids and/or, at least one representative of the group of trace elements and minerals and/or at least one representative of the group of vitamins and/or at least one representative of the group of bioactive plant substances, e.g. polyphenoles, bioflavonoids or dietary fiber and/or at least one amino acid and/or amino acid derivative, product A and/or) product B optionally additionally containing soy lecithin, with the proviso that product A and product B differ from each other in their quantitative and/or their material composition. The preparation can be used as a food supplement (dietary supplement) or as a drug.

17 Claims, No Drawings

TWO-PHASE PREPARATION

This application is the national phase under 35 U.S.C. §371 of prior PCT International Application No., PCT/EP96/03329, which has an International filing date of Jul. 29, 1996, which designated the United States of America, the entire contents of which are hereby incorporated by reference.

The invention relates to a two-phase preparation for use at differential times containing a product A for the first phase and a product B for the second phase which comprise, independently of each other, at least one representative of the unsaturated fatty acids and/or at least one representative of the group of trace elements and minerals and/or at least one representative of the group of vitamins and/or at least one representative of the group of bioactive plant substances, e.g. polyphenoles, bioflavonoids or dietary fiber, and/or at least one amino acid and/or amino acid derivative, product A and/or product B optionally additionally containing soy lecithin, with the proviso that product A and product B differ from each other in their quantitative and/or their material composition. The preparation can be used as a food supplement (dietary supplement) or as a drug.

In particular, the invention relates to a two-phase preparation for use at differential times comprising a product A and a product B which include, independently of each other, at least one representative of the unsaturated fatty acids, one representative of the group of trace elements and minerals and one representative of the group of vitamins, product A and/or product B optionally additionally containing soy lecithin, and/or at least one representative of the group of bioactive plant substances and/or at least one amino acid and/or amino acid derivative which is used as a food supplement (dietary supplement).

It is generally known that the nutrients carbohydrates as well as the dietary fats are mainly used to cover the body's energy requirement. Proteins are important building components for cells and endogenous active substances such as enzymes and certain hormones. Polyunsaturated fatty acids, vitamins, minerals and trace elements as well as bioactive plant substances such as flavonoids are becoming more and more important for health and fitness.

Vitamins, minerals and trace elements, polyunsaturated fatty acids and bioactive plant substances such as flavonoids are essential regulators in the metabolism and nutrients protecting health. However, a one-sided diet, stringent weight reduction diets, preference of high-calorie foods of low nutrient density and the high degree of processing of many foods but also the partial impoverishment of the soils with respect to important minerals make an optimal supply with all the necessary nutrients difficult. In addition, due to adverse environmental effects, smoking, consuming alcohol and medicaments as well as stress, there is an increased demand of some essential nutrients, for example magnesium, zinc, vitamin E, vitamin C, B-type vitamins and beta carotene. A food complementary nutrient substitution therefore contributes to a sufficient supply of nutrients, an optimal protection of health and well-being, as does a well-balanced nutrition which is high-roughage and low-fat. The reference "Empfehlungen für die Nährstoffzufuhr" [Recommendations for the supply with nutrients], Deutsche Gesellschaft für Ernährung, 5th edition, 1991, Umschau Verlag, Frankfurt/Main, describes recommendations for the body's supply with nutrients.

Vitamins are essential nutritional components which are more or less indispensable for the normal body functions of heterotroph organisms and which have to be supplied as required since they are only available either from outside sources or under the influence of milieu factors (e.g. intestinal flora). Their specific biocatalytic effect is to replace the active component of enzymes which is subject to metabolical consumption. From science it is for example known that B-type vitamins participate in the intermediary metabolism as coenzymes and that vitamins C, E and beta carotene mainly function as antioxidants. A deficiency due to an insufficient supply or resorption, a disorder of the intestinal flora or the metabolism, the effects of antivitamins or an increased consumption lead to hypovitaminosis and avitaminosis.

Furthermore, minerals and trace elements are essential regulators in the metabolism. Calcium is the most important mineral building substance for bones and teeth. A sufficient supply of calcium up until the age of 30 is the best protection against osteoporosis during old age. After that, sufficient food calcium ensures that the depot in the bones is not unduly strained. For women calcium is often a critical nutrient. Zinc, magnesium and B-type vitamins are high-performance elements which activate enzymes and thus allow the metabolism of carbohydrates, fats and proteins. Silicon favorably contributes to the stability and maintenance of skin, hair and nails. Furthermore, it is scientifically undisputed that zinc fulfills an essential function in the body's immune system and the skin metabolism.

Polyunsaturated fatty acids from purely vegetal sources such as for example evening primrose oil and linseed oil, contain linolic acid and $\alpha$- and $\gamma$-linolenic acid, which are important starting substances for biologically active regulators, as for example eicosanoids and prostaglandins, and ensure a healthy equilibrium in the metabolism. Eicosanoids and prostaglandins, also referred to as tissue hormones, are currently being studied extensively by scientists for their health stabilizing effects. The favorable effect of polyunsaturated fatty acids on the cholesterol metabolism and healthy skin function as well as on inflammatory processes is known. It is furthermore known that polyunsaturated fatty acids of the type of $\omega$-3 (icosapentenoic acid, $\alpha$-linolenic acid) and $\omega$-6 (linolic acid, $\gamma$-linolenic acid) fatty acids have a favorable effect on migraine, rheumatism, neurodermatitis, psoriasis, premenstrual syndrome and regeneration processes induced by physical strain during exercise (cf. A. Berg, D. König, H. Schlachter, J. Keul, *Deutsche Zeitschrift für Sportmedizin* [German Magazine of Sports Medicine], Volume 44 (1993), Special Issue, and literature cited therein).

Carrot, broccoli and citrus extracts are natural sources of vitamins and minerals and contain the so-called secondary plant substances, which are also referred to as bioactive plant substances in the special branch of science whose significance has been recognized and is now being examined as well. These natural plant substances also include bioflavonoids which effectively support the impact of vitamin C with respect to the power of resistance, the vascular walls and the connective tissue. It is also known that bioflavonoids have antioxidant properties and therefore synergistically complement the effect of vitamins C, E and beta carotene. Green tea as well is an excellent source of these vegetal antioxidants (e.g. polyphenols) (cf. B. Watzl, C. Leitzmann *Bioaktive Substanzen in Lebensmitteln* [Bioactive substances in foodstuffs], Hippokrates Publishing House, Stuttgart, 1995).

In addition to their function as building blocks for proteins, amino acids are precursors of biologically effective compounds, for example serotonin, growth and stress hormones. They are also said to have anticatabolic properties (cf. in this connection K. R. Geiβ, M. Hamm *Handbuch Sporternährung* [*Handbook of sports nutrition*], Rowohlt Publishing House, 1992).

A great number of food supplements are commercially available which contain individual vitamins (e.g. vitamin E preparations) or combinations thereof (e.g. multivitamin preparations) and/or individual minerals and trace elements (e.g. magnesium or iron preparations) or combinations thereof (e.g. multimineral capsules). There are also preparations with polyunsaturated fatty acids alone or in combination with vitamins and minerals. For example, a preparation may contain many different vitamins and some selected minerals which cover the daily requirement of these nutrients.

Another commercially available preparation is characterized as a supplementary balanced diet for covering a specific increased demand of essential nutrients, in particular in view of a purpose-specific nutrition, for example after a heart attack or by-pass surgery, when the strained situation of the metabolism requires compensation. As a daily requirement, this so-called dietary foodstuff consists of a bag with 9 tablets or capsules whereby the contents of the bag are usually taken with or after a meal, whereby, however, it is also possible to take the individual capsules or tablets with meals in any desired order over the whole day. The daily requirement of this preparation comprises essential vitamins such as vitamin A, B1, B2, B3, B6, B12, C, E, D3, K and beta carotene, trace elements such as iron, zinc, manganese, chromium, magnesium and selenium, and specific essential fatty acids. However, this dietary foodstuff contains amounts of vitamins larger than the basic recommended daily allowance for a healthy adult.

Most of the commercially available food supplements are presented in the form of capsules or tablets and are usually taken independently of the time of day.

So far, food supplements have generally been intended to cover the nutritional requirements resulting from an insufficient nutrition. Despite the large number of food supplements, no optimal solution for an appropriate supply has yet been provided which sufficiently takes into account the scientific findings. From science, it is known that in contrast to a combination of many vitamins and minerals in one single form of administration, spreading the administration of these substances makes more sense from a physiological point of view. Compared to a high dosage of nutrients, the lower individual doses are more readily available. It is also known that the simultaneous intake of minerals and trace elements in a single form of administration can adversely affect the resorption of the individual components. Amongst others, magnesium and calcium as well as iron, zinc and selenium adversely affect each other.

In many known preparations, the composition of the ingredients does not always make sense as the simultaneous administration of all essential nutrients can reduce the availability of the individual components (for example, magnesium is not absorbed as well if the calcium content of a single dose is markedly higher than the magnesium content). Also, due to the prooxidative properties of iron, undesired reactions can take place between iron and polyunsaturated fatty acids.

In one of the above-mentioned commercially available preparations, the user has to take nine capsules or tablets a day with one or more meals. However, an acceptable daily dose should not exceed three individual doses each day (e.g. one to three capsules a day).

The human metabolism goes through day and night phases. It is assumed that these day and night phases also influence the nutrient balance, nutrient absorption and requirements of the body. It is an object of the present invention to provide a reasonably composed two-phase preparation wherein the daily supply of nutrients is distributed with respect to activating nutritional principles to the first half of the day and with respect to regenerative nutritional principles to the second half of the day. Another object of the present invention is to provide a two-phase preparation tailored to the needs of specific target groups. The two-phase preparation is to be used as a dietary supplement and/or a drug.

One of the objects of the present invention is achieved by providing a two-phase preparation for use at differential times comprising a product A for the first phase (active phase) and a product B for the second phase (regenerative phase) wherein the product A comprises a) at least one representative of the unsaturated fatty acids and/or b) at least one representative of the group of trace elements and minerals and/or c) at least one representative of the group of vitamins and/or d) at least one representative of the bioactive plant substances and/or e) at least one amino acid and/or amino acid derivative and the product B comprises a) at least one representative of the unsaturated fatty acids and/or b) at least one representative of the group of trace elements and minerals and/or c) at least one representative of the group of vitamins and/or d) at least one representative of the group of bioactive plant substances and/or e) at least one amino acid and/or amino acid derivative with the proviso that product A and product B differ from each other in their quantitative and/or material composition.

In a preferred embodiment, the present invention also provides a two-phase preparation for use at differential times comprising a product A for the first phase and a product B for the second phase wherein the product A comprises a) at least one representative of the unsaturated fatty acids, b) at least one representative of the group of trace elements and minerals and c) at least one representative of the group of vitamins and the product B comprises a) at least one representative of the unsaturated fatty acids, b) at least one representative of the group of trace elements and minerals and c) at least one representative of the group of vitamins.

In an especially preferred embodiment, a two-phase dietary supplement for use at differential times is provided comprising a product A for the first phase and a product B for the second phase wherein the product A and the product B each comprise, independently of each other, a) at least one representative of the unsaturated fatty acids, b) at least one representative of the group of trace elements and minerals and c) at least one representative of the group of vitamins.

In another preferred embodiment, the product A and/or the product B can additionally comprise soy lecithin. Soy lecithin is preferably added in an amount of 1 to 4% by weight, and most preferably 5 to 20% by weight, based on the sum of all active ingredients of product A and B, respectively.

In a further embodiment, the product A and/or the product B of the preferred embodiments can additionally comprise at least one representative of the group of bioactive plant substances.

In a further embodiment, the product A and/or the product B of the preferred embodiments can additionally comprise amino acids and/or amino acid derivatives, also in combination with other active ingredients of the present invention.

The term "for use at differential times" means that the product A is to be applied or to provide its effect at the beginning of the day phase or active phase and the product B at the beginning of the night phase or regenerative phase of the human metabolism. Preferably, the product A is administered in the morning and the product B in the evening of the same day.

The term "two-phase" refers to the day or active phase as first phase (first half of the day) and to the night or regenerative phase as the second phase (second half of the day) of the human metabolism.

Product A and product B of the present invention differ from each other in their quantitative and/or material composition.

The formulations of the present invention preferably take into account synergistic effects, e.g. in the case of vitamin C and bioflavonoids as well as vitamin C and polyunsaturated fatty acids.

In the two-phase preparation of the present invention the products A and B can comprise all known representatives of the vitamins. In particular, the product A of the two-phase preparation preferably comprises the vitamins C and E as antioxidants (cell protection vitamins), and the vitamins B1, B2, B6, B12, pantothenic acid, beta carotene and niacin, and the product B preferably comprises the vitamins B1, B2, B6, B12, pantothenic acid, niacin and folic acid and biotin as metabolism regulators in the sense of coenzymes of the carbohydrate, fat and protein metabolism.

In the preferred embodiments of the two-phase preparation of the present invention, the content of vitamins is preferably 1 to 70% by weight in product A and 0.5 to 50 by weight in product B, based on the sum of all active ingredients of product A and B, respectively. In a more preferred embodiment, product A comprises 5 to 50% by weight of vitamins, especially preferred 20 to 45% by weight, and product B comprises 1 to 40% by weight of vitamins, especially preferred 1 to 35% by weight. The vitamins are added both in natural form as extracts (e.g. D-α-tocopherol) and in synthetic form. (e.g. B-type vitamins), which, however, does not influence the effectivity of the vitamins.

Representatives of the group of trace elements and minerals in the two-phase preparation of the present invention comprises all known minerals and trace elements. In a preferred embodiment, the product A of the two-phase preparation in particular comprises zinc, magnesium and chromium and the product B comprises silicon, magnesium, zinc and calcium. The content of minerals and trace elements in the preferred embodiments is preferably 1 to 80% by weight in product A and product B, more preferred 2 to 50% by weight in product A, particularly preferred 5 to 30% by weight, and 2 to 70% by weight in product B, particularly preferred 3 to 60% by weight, based on the sum of all active ingredients of product A and B, respectively. The trace elements are preferably added in the form of chromium, zinc and silicon yeasts -or other organic compounds. The major elements, such as for example magnesium and calcium, are present in the form of inorganic salt compounds or organic compounds. For instance, magnesium or calcium are added as magnesium or calcium carbonate.

In the two-phase preparation of the present invention all known unsaturated fatty acids can be used. Preferably, the unsaturated fatty acids contained in vegetable and animal oils are used. Polyunsaturated fatty acids from vegetal or animal sources are essential precursors of important metabolism regulators (eicosanoids and prostaglandins). In the preferred embodiments of the two-phase preparation, the unsaturated fatty acids are preferably present in product A in an amount of 5 to 90% by weight, more preferably 10 to 70% by weight and particularly preferred 30 to 60% by weight, and in product B in a preferred amount of 1 to 90% by weight, more preferably 3 to 85% by weight and particularly preferred 5 to 80% by weight, based on the sum of all active ingredients of product A and B, respectively. Examples of preferred purely vegetal sources of unsaturated fatty acids include evening primrose oil, linseed oil, olive oil and wheat germ oil and preferred animal sources include for example fish oil.

Optionally, the two-phase preparation of the present invention can comprise all known bioactive plant substances.

The bioactive plant substances used in the present invention in particular comprise carotenoids, phytosterols, saponins, polyphenols, flavonoids, terpenes, phytoestrogens, sulfides, phytic acid and dietary fiber. Of the above-mentioned bioactive plant substances, polyphenols, flavonoids and bioflavonoids and dietary fiber are most preferably used in the present invention. Bioflavonoids of natural sources such as citrus fruit flavonoids are especially preferred in the two-phase preparation. In the preferred embodiments, the bioactive plant substances can preferably be present in product A and/or product B of the two-phase preparation in an amount of 1 to 50% by weight, more preferably 1 to 30% by weight and most preferably 1 to 20% by weight, based on the sum of all active ingredients of product A and B, respectively. Preferred natural sources of the vasco-active and antioxidant bioflavonoids are carrot, broccoli and citrus extracts as well as green tea.

The two-phase preparation of the present invention can optionally contain all known amino acids and amino acid derivatives. Preferably, in the two-phase preparation mixtures of amino acids and/or amino acid derivatives are used, including the amino acids arginine, ornithine, leucine, isoleucine, valine and tryptophan and the amino acid derivatives taurine and carnitine. Further preferred are mixtures of amino acids and amino acid derivatives with vitamin B6 and coenzyme $Q_{10}$ to promote regeneration and anabolism during the night phase. In the preferred embodiments, the amino acids can preferably be present individually or in the form of mixtures in product A and/or product B of the two-phase preparation in an amount of 10 to 95% by weight, more preferably 50 to 90% by weight and most preferably 80 to 90% by weight, based on the sum of all active ingredients of product A and B, respectively. The amino acids and their derivatives are preferably added in pure form.

Optionally, the two-phase preparation of the present invention can comprise all known adjuvants, additives, carriers and solvents. Preferred examples thereof include milk fat, hydrogenated, partly hydrogenated and unhydrogenated soybean fat, soybean oil, walnut butter, glycerin, gelatin, sorbitol solution or dry substance, iron oxide, titanium dioxide, patent blue, quinoline yellow, ponceau and water.

The manufacture of the two-phase preparation of the present invention can be carried out in the usual manner known to the person skilled in the art by combining the active ingredients with suitable non-toxic, inert, pharmaceutically acceptable solid or liquid carriers and optionally the usual additives, adjuvants and solvents to a galenic form of administration. Methods for manufacturing galenic forms of administration, e.g. soft gelatin capsules, are for example described in H. Sucker, P. Fuchs, P. Speiser, *Pharmazeutische Technologie* [Pharmaceutical Technology], $2^{nd}$ edition 1991, Georg Thieme Verlag, Stuttgart; R. Voigt, *Lehrbuch der pharmazeutischen Technologie* [Handbook of Pharmaceutical Technology], Chemie Verlag 1976; Fahrig and Hofer *Die Kapsel* [The Capsule], Wissenschaftliche Verlagsgesellschaft 1982; Remington's Pharmaceutical Sciences, $15^{th}$ edition 1975, Mack Publishing Company, Easton, Pa.

For the two-phase preparation of the present invention all known forms of application such as capsules, tablets, dragées and solutions etc. and all known ways of application are possible. In particular, however, oral administration is preferred, the preferred forms of application being soft gelatin capsules, ampoules for drinking, small bags (small ampoules) and ready-to-drink liquids. If, for instance, the two-phase preparation of the present invention is provided in soft gelatin capsules, the dosage is preferably such that the product A, which contains the reasonable nutrients for the day phase or active phase, is enclosed in a capsule A which should preferably be administered in the morning. The product B, which contains the reasonable nutrients for the night phase or regenerative phase, is enclosed in a capsule B which should preferably be administered in the evening. Both capsules A and B contain the total dosage for the day and the night phases of one day, respectively. It is suggested to administer per day a capsule A in the morning and a capsule B in the evening. The two-phase preparation of the present invention can be provided as a kit, comprising for example the same number of capsules A and capsules B. Further forms of application can be ampoules for drinking and bags. However, it is also possible to provide product A and product B modified in a single form of application such that the active ingredients of product A and product B are released at different times (i.e. depot form).

The present invention is explained in more detail by means of examples.

EXAMPLE 1

This example comprises a two-phase preparation for use at differential times, which is especially tailored to the female organism, as a dietary supplement. The compositions of capsule A and capsule B given in Table I were obtained in the usual manner known to the person skilled in the art and enclosed in soft gelatin capsules by means of common methods. Additionally, the preparation may contain known additives, adjuvants and carriers, and solvents.

TABLE I

| Capsule A | |
|---|---|
| 10 mg | carrot extract |
| 200 mg | evening primrose oil |
| 100 mg | linseed oil |
| 50 mg | soy lecithin |
| 5 mg | beta carotene in the form of a 30% beta carotene suspension |
| 30 mg | vitamin E |
| 200 mg | vitamin C |
| 200 mg | zinc yeast (10 mg Zn/g yeast) |
| 50 mg | magnesium |
| 50 mg | flavonoids from citrus fruit |

TABLE I-continued

| Capsule B | |
|---|---|
| 20 mg | broccoli extract |
| 200 mg | evening primrose oil |
| 100 mg | linseed oil |
| 5 mg | vitamin E |
| 100 mg | silicon yeast (30 mg Si/g yeast) |
| 300 mg | calcium |
| 3 mg | vitamin B1 |
| 3 mg | vitamin B2 |
| 5 mg | vitamin B6 |
| 8 mg | pantothenic acid |
| 10 mg | niacin |
| 5 μg | vitamin B12 |
| 150 μg | folic acid |
| 100 μg | biotin |
| 100 mg | zinc yeast (10 mg Zn/g yeast) |
| 50 mg | flavonoids from citrus fruit |

EXAMPLE 2

This example comprises a two-phase preparation for use at differential times, which is especially tailored to the male organism, as a dietary supplement. The compositions of capsule A and capsule B given in Table II were obtained in the usual manner known to the person skilled in the art and enclosed in soft gelatin capsules by means of common methods. Additionally, the preparation may contain known additives, adjuvants and carriers, and solvents.

TABLE II

| Capsule A | |
|---|---|
| 300 mg | fish oil (icosapentenoic acid) |
| 100 mg | linseed oil |
| 100 mg | soy lecithin |
| 36 mg | vitamin E |
| 200 mg | vitamin C |
| 5 mg | beta carotene |
| 100 mg | magnesium |
| 100 mg | chromium yeast |
| 50 mg | bioflavonoids |
| Capsule B | |
| 300 mg | olive oil |
| 300 mg | wheat germ oil |
| 100 mg | magnesium |
| 4.5 mg | vitamin B1 |
| 5 mg | vitamin B2 |
| 5 mg | vitamin B6 |
| 8 mg | pantothenic acid |
| 10 mg | niacin |
| 5 μg | vitamin B12 |
| 200 mg | zinc yeast (10 mg Zn/g yeast) |
| 100 mg | green tea extract |

EXAMPLE 3

This example comprises a two-phase preparation for use at differential times, which is especially tailored to the organism of athletes, as a dietary supplement. The compositions of capsule A and bag B given in Table III were obtained in the usual manner known to the person skilled in the art. Additionally, the formulation may contain known additives, adjuvants and carriers, and solvents.

TABLE III

Capsule A

| | |
|---|---|
| 200 mg | magnesium |
| 250 mg | linseed oil |
| 250 mg | evening primrose oil |
| 36 mg | vitamin E |
| 225 mg | vitamin C |
| 6 mg | beta carotene |
| 4.5 mg | vitamin B1 |
| 5 mg | vitamin B2 |
| 5 mg | vitamin B6 |
| 8 mg | pantothenic acid |
| 10 mg | niacin |
| 5 µg | vitamin B12 |
| 200 mg | zinc yeast (10 mg Zn/g yeast) |
| 100 mg | chromium yeast |
| 100 mg | flavonoids from citrus fruit |

Product B (bag)
Mixture of amino acids and amino acid derivatives with vitamin B6 and coenzyme $Q_{10}$ to promote regeneration and anabolism during the night phase and to promote the fat metabolism/lipolysis.

| | |
|---|---|
| 100 mg | zinc yeast (10 mg Zn/g yeast) |
| 100 mg | magnesium |
| 200 mg | wheat germ oil |
| 50 mg | flavonoids from citrus fruit |
| 2000 mg | mixture of amino acids and amino acid derivatives with vitamin B6 and coenzyme $Q_{10}$ |

What is claimed is:

1. A method for supplementing diet or drug administration at differential times comprising two-phases, wherein a supplemental preparation A is administered during the day phase or active phase and a supplement preparation B is administered during the night phase or regenerative phase, wherein preparation A comprises an activating component selected from the group consisting of:
  a) at least one representative of the unsaturated fatty acids,
  b) at least one representative of the group of trace elements and minerals,
  c) at least one representative of the group of vitamins,
  d) at least one representative of the bioactive plant substances,
  e) at least one amino acid, amino acid derivative, or combination thereof, and
  f) mixtures thereof,
and preparation B comprises a regenerating component selected from the group consisting of:
  a) at least one representative of the unsaturated fatty acids,
  b) at least one representative of the group of trace elements and minerals,
  c) at least one representative of the group of vitamins,
  d) at least one representative of the bioactive plant substances,
  e) at least one amino acid, amino acid derivative, or combination thereof, and
  f) mixtures thereof,
with the proviso that preparation A and preparation B differ from each other in their material composition, and with the further proviso that the components in preparation A and preparation B are further selected with respect to synergistic and antagonistic effects, respectively.

2. A method for supplementing diet or drug administration at differential times comprising two-phases, wherein a supplement preparation A is administered during the day phase or active phase, and a supplemental preparation B is administered during the night phase or regenerative phase, wherein preparation A comprises:
  a) at least one representative of the unsaturated fatty acids,
  b) at least one representative of the group of trace elements and minerals, and
  c) at least one representative of the group of vitamins, wherein at least one of said representatives is an activating component,
and preparation B comprises:
  a) at: least one representative of the unsaturated fatty acids,
  b) at least one representative of the group of trace elements and minerals, and
  c) at least one representative of the group of vitamins, wherein at least one of said representatives is a regenerating component,
with the proviso that preparation A and preparation B differ from each other in their material composition, and with the further proviso that the components in preparation A and preparation B are further selected with respect to synergistic and antagonistic effects, respectively.

3. The method according to claim 1 or 2, wherein preparation A or preparation B or both preparations additionally comprise soy lecithin.

4. A method according to claim 2, wherein preparation A or preparation B or both preparations additionally comprise at least one representative of the group of bioactive plant substances.

5. The method according to claim 2, wherein preparation A or preparation B or both preparations additionally comprise a member selected from the group consisting of amino acid, amino acid derivative, and mixtures thereof.

6. The method according to claim 2, wherein the preparation A comprises the component a) in an amount of 5 to 90% by weight, the component b) in an amount of 1 to 80% by weight and the component c) in an amount of 1 to 70% by weight, and preparation B comprises the component a) in an amount of 1 to 90% by weight, the component b) in an amount of 1 to 80% by weight and the component c) in an amount of 0.5 to 50% by weight, based on the sum of all active ingredients of preparation A and B, respectively.

7. The method according to claim 2, wherein the preparation A comprises the component a) in an amount of 30 to 60% by weight, the component b) in an amount of 5 to 30% by weight and the component c) in an amount of 20 to 45% by weight, and preparation B comprises the component a) in an amount of 5 to 80% by weight, the component b) in an amount of 3 to 60% by weight and the component c) in an amount of 1 to 35% by weight, based on the sum of all active ingredients of preparation A and B, respectively.

8. The method according to claim 1 or 2, wherein preparation A or preparation B or both preparations additionally comprise 1 to 40% by weight of soy lecithin, based on the sum of Wall active ingredients of preparation A and B, respectively.

9. The method according to claim 1 or 2, wherein preparation A or preparation B or both preparations additionally comprise 1 to 50% by weight of at least one representative of the group of bioactive plant substances, based on the sum of all active ingredients of preparation A and B, respectively.

10. The method according to claim 1 or 2, wherein the unsaturated fatty acids of preparation A and preparation B are unsaturated fatty acids contained in vegetal or animal oils.

11. The method according to claim 1 or 2, wherein the trace elements and minerals of preparation A and preparation B are zinc, magnesium, calcium, silicon and chromium.

12. The method according to claim 1 or 2, wherein the vitamins of preparation A and preparation B are the vitamins B1, B2, B6, B12, C, E, pantothenic acid, niacin, folic acid and biotin.

13. The method according to claims 1 or 4, wherein the bioactive plant substances of preparation A or preparation B are the bioflavonoids contained in carrot, broccoli and citrus extracts and green tea.

14. The method according to claim 1 or 5, wherein preparation A or preparation B or both preparations contain arginine, ornithine, leucine, isoleucine, valine and tryptophan as amino acids and/or taurine and carnitine as amino acid derivatives, either individually or as a combination of at least two of said amino acids and/or amino acid derivatives.

15. A kit containing a two-phase food supplement preparation comprising a preparation A and a preparation B as defined in claim 1 or 2.

16. A kit containing a two-phase drug preparation comprising a preparation A and a preparation B as defined in claim 1 or 2.

17. A method for supplementing diet or drug administration at differential times comprising two-phases, wherein a supplement preparation A is administered during the day phase or active phase and a supplement preparation B is administered during the night phase or regenerative phase, wherein the preparation A comprises:

a) at least one representative of the group of trace elements and minerals, b) at least one representative of the group of vitamins, and c) at least one representative of the bioactive plant substances, wherein at least one said representative is an activating component, and preparation B comprises a) at least one representative of the group of trace elements and minerals, b) at least one representative of the group of vitamins, and c) at least one representative of the bioactive plant substances, wherein at least one of said representatives is a regenerating component, with the proviso that preparation A and preparation B differ from each other in their material composition, and with the further proviso that the components in preparation A and preparation B are further selected with respect to synergistic and antagonistic effects, respectively.

\* \* \* \* \*